United States Patent
Kraizer et al.

(10) Patent No.: US 7,585,283 B2
(45) Date of Patent: Sep. 8, 2009

(54) DEVICE AND METHOD FOR EXAMINING A BODY LUMEN

(75) Inventors: Yehudit Kraizer, Kiryat Tivon (IL); Raphael Rabinovitz, Raanana (IL); Yoram Sela, Raanana (IL)

(73) Assignee: Given Imaging Ltd., Yoqneam (IL)

(*) Notice: Subject to any disclaimer, the term of this patent is extended or adjusted under 35 U.S.C. 154(b) by 628 days.

(21) Appl. No.: 10/988,614

(22) Filed: Nov. 16, 2004

(65) Prior Publication Data
US 2005/0063906 A1  Mar. 24, 2005

Related U.S. Application Data

(63) Continuation-in-part of application No. 10/192,861, filed on Jul. 11, 2002, now Pat. No. 7,083,578.

(30) Foreign Application Priority Data

Jul. 12, 2001 (IL) .................. 144296
Dec. 16, 2001 (IL) .................. 147126

(51) Int. Cl.
*A61B 5/117* (2006.01)
*A61B 5/103* (2006.01)
*A61K 9/52* (2006.01)

(52) U.S. Cl. .................. 600/593; 424/457

(58) Field of Classification Search .......... 600/587, 600/593, 101, 160, 167, 178; 604/892.1, 604/890.1; 424/463, 464, 466, 468, 470, 424/400, 451–453, 501, 426, 78.35, 78.37, 424/472, 457, 458, 465; 359/642; 521/99, 521/142, 149, 136, 134, 186, 189; 623/1.42

See application file for complete search history.

(56) References Cited

U.S. PATENT DOCUMENTS

| 3,971,362 A | 7/1976 | Pope et al. |
| 4,177,800 A | 12/1979 | Enger |
| 4,239,040 A | 12/1980 | Hosoya et al. |
| 4,246,784 A | 1/1981 | Bowen |
| 4,278,077 A | 7/1981 | Mizumoto |
| 4,431,005 A | 2/1984 | McCormick |
| 4,439,197 A | 3/1984 | Honda et al. |
| 4,681,093 A | 7/1987 | Ono et al. |
| 4,689,621 A | 8/1987 | Kleinberg |

(Continued)

FOREIGN PATENT DOCUMENTS

DE  34 40 177  5/1986

(Continued)

OTHER PUBLICATIONS

European Search report of Application No. EP 05 07 7574, dated Jun. 19, 2006.

(Continued)

*Primary Examiner*—Max Hindenburg
*Assistant Examiner*—Brian Szmal
(74) *Attorney, Agent, or Firm*—Pearl Cohen Zedek Latzer, LLP

(57) ABSTRACT

A device and method is described for enabling an examining device to pass through an abnormally configured body lumen. The device may pass through a body lumen while maintaining an initial dimension. Upon encounter with an abnormally configured body lumen, the device may be depleted and take on a final dimension after a predetermined time period, regardless of its current orientation with respect to the body lumen, so that the device may pass through and vacate the abnormally configured body lumen shortly after the predetermined time period may have elapsed.

27 Claims, 2 Drawing Sheets

U.S. PATENT DOCUMENTS

| | | | |
|---|---|---|---|
| 4,784,155 A | 11/1988 | Mills | |
| 4,844,076 A | 7/1989 | Lesho et al. | |
| 4,915,113 A | 4/1990 | Holman | |
| 4,936,823 A | 6/1990 | Colvin et al. | |
| 5,279,607 A | 1/1994 | Schentag et al. | |
| 5,330,427 A | 7/1994 | Weissenburger | |
| 5,395,366 A | 3/1995 | D'Andrea et la. | |
| 5,558,640 A | 9/1996 | Pfeiler et al. | |
| 5,604,531 A | 2/1997 | Iddan et al. | |
| 5,697,384 A | 12/1997 | Miyawaki et al. | |
| 5,782,747 A | 7/1998 | Zimmon | |
| 5,819,736 A | 10/1998 | Avny et al. | |
| 5,906,579 A | 5/1999 | Vander Salm et al. | |
| 5,972,389 A | 10/1999 | Shell et al. | |
| 5,976,571 A | 11/1999 | Crison et al. | |
| 5,993,378 A | 11/1999 | Lemelson | |
| 6,172,640 B1 | 1/2001 | Durst et al. | |
| 6,188,355 B1 | 2/2001 | Gilboa | |
| 6,240,312 B1 | 5/2001 | Alfano et al. | |
| 6,346,269 B1 * | 2/2002 | Hsiao et al. | 424/472 |
| 6,599,284 B2 * | 7/2003 | Faour | 604/892.1 |
| 7,195,778 B2 | 3/2007 | Fleshner-Barak et al. | |
| 2001/0035902 A1 | 11/2001 | Iddan et al. | |
| 2001/0038831 A1 | 11/2001 | Park et al. | |
| 2001/0045899 A1 | 11/2001 | Hoek | |
| 2002/0103417 A1 | 8/2002 | Gazdzinski | |
| 2002/0198470 A1 | 12/2002 | Imran et al. | |
| 2003/0144570 A1 | 7/2003 | Hunter et al. | |
| 2003/0167000 A1 | 9/2003 | Mullick et al. | |
| 2003/0208107 A1 | 11/2003 | Refael | |
| 2004/0066262 A1 | 4/2004 | Wenner | |
| 2004/0176684 A1 | 9/2004 | Tabuchi et al. | |
| 2006/0061472 A1 | 3/2006 | Lovoi et al. | |
| 2006/0136051 A1 * | 6/2006 | Furst et al. | 623/1.42 |

FOREIGN PATENT DOCUMENTS

| | | |
|---|---|---|
| DE | 10018341 | 4/2000 |
| DE | 10121191 | 4/2001 |
| EP | 0 3 44 770 | 12/1989 |
| JP | 4109927 | 4/1992 |
| JP | 1992-144533 | 5/1992 |
| JP | 5015515 | 1/1993 |
| JP | 6285044 | 10/1994 |
| WO | WO 88/00449 | 1/1988 |
| WO | WO 01/50941 | 7/2001 |
| WO | WO 01/65995 | 9/2001 |
| WO | WO 01/78836 | 10/2001 |
| WO | WO 02/087493 | 11/2002 |
| WO | WO 03/005877 | 1/2003 |
| WO | WO 03/005951 | 1/2003 |

OTHER PUBLICATIONS

The Radio Pill, Rowlands, et al., British Communications and Electronics, Aug. 1960, pp. 598-601.

Wellesley company sends body monitors into space—Crum, Apr. 1998.

Wireless transmission of a color television moving image from the stomach using a miniature CCD camera, light source and microwave transmitter Swain CP, Gong F, Mills TN. Gastrointest Endosc 1997;45:AB40.

BBC News Online—Pill camera to 'broadcast from the gut', Feb. 21, 2000, www.news.bbc.co.uk.

W. Weitschies, R. Kotitz, D. Cordin, L. Trahms, High-Resolution Monitoring of the Gastrointestinal Transit of a Magnetically Marked Capsule, (1997), Journal of Pharmaceutical Sciences, vol. 86, No. 11, pp. 1218-1222.

Transit times for the Capsule Endoscope, Gastrointestinal Endoscopy 2001; 53:AB122.

International Search Report for International Application No. PCT/IL02/00562, Mar. 28, 2008.

Office Action for Australian Application No. 2008202321 dated Apr. 30, 2009.

* cited by examiner

DEVICE AND METHOD FOR EXAMINING A BODY LUMEN

CROSS-REFERENCE TO RELATED APPLICATIONS

This application is a continuation-in-part of U.S. patent application Ser. No. 10/192,861, entitled "Device and Method for Examining a Body Lumen", filed on Jul. 11, 2002 now U.S. Pat. No. 7,083,578, which is hereby incorporated by reference in its entirety, and which claims priority and benefit from (a) Israeli Patent Application Number 144296, entitled "A Device and Method for Testing a Body Lumen Configuration", filed on Jul. 12, 2001, which is hereby incorporated by reference in its entirety, and (b) Israeli Patent Application Number 147126, entitled "A Device and Method for Testing a Body Lumen Configuration", filed on Dec. 16, 2001, which is hereby incorporated by reference in its entirety.

FIELD OF THE INVENTION

The present invention relates to a device and method for examining a body lumen. The device and method may be useful, inter alia, in detecting abnormalities in a body lumen configuration.

BACKGROUND OF THE INVENTION

Tubular organs in the body may have a convoluted cavity configuration. The gastrointestinal tract, for example, starts from the oral cavity and proceeds through the esophagus, stomach, duodenum and small intestine, which may be a long tube that may fold many times to fit inside the abdomen. The small intestine is connected to the large intestine, which begins with the cecum, a small saclike evagination, then continues with the ascending colon, transverse colon, descending colon and the sigmoid (S-shaped) colon to the rectum. These body lumens may suffer from pathologies, which may affect the anatomy or configuration of the lumen. For example, strictures, narrowing or closure of a normally configured lumen may be caused by calcification or by the presence of scar tissue or a tumor. Strictures of the esophagus may be a common complication of chronic gastroeosophagaeal reflux disease (GERD). Acute, complete obstruction of the esophagus may occur when food may be lodged in the esophageal stricture. Endoscopy may usually be employed to retrieve the food and relieve the obstruction.

Methods for diagnosis of body lumens may usually be symptom related or invasive. Non-invasive techniques of diagnosing the gastrointestinal (GI) tract may include utilizing solid non-degradable ingestible autonomous electronic or magnetically marked capsules. These autonomous capsules may include capsules for measuring motility in the GI tract, gastric pH (such as the Heidelberg capsule) and in-vivo temperature (such as the CoreTemp™ capsule). Also, gastric transit may be measured by using biomagnetic measuring equipment such as a magnetically marked capsule, which is a solid non-degradable oral dosage form containing powdered magnetite encapsulated in silicone rubber (W. Weitschies, R. Kotitz, D. Cordin, L. Trahms, (1997), *J Pharm Sci,* 86:1218-1222). Such capsules may typically be propelled through the GI system by peristalsis. These non-invasive methods may enable reaching parts of the intestine, for example, distal parts of the small intestine aejunum and ileum) that may not be reachable by other methods. However, in rare cases of severe strictures in the GI tract, swallowing of a solid bolus (such as an electronic or magnetically marked capsule) may cause obstruction of the GI tract.

Non-invasive methods for detection of strictures, specifically in the GI tract, usually include x-ray series that may be based on intake of x-ray opaque (radio-opaque) material (barium sulphate, gastrographine, or others), for example a barium pill (solid bolus) that dissolves rapidly for testing strictures in the esophagus. The material may reside for some time on the walls of the GI tract, enabling examination of the x-ray images of the GI tract. This technique may have several drawbacks, namely, low detection rate and exposure to x-ray radiation.

In-vivo devices, pills, or other medical systems may need to pass through the GI tract. However, it may be difficult to predict if such devices, pills, or systems may achieve safe passage through the GI tract, short of actually attempting to pass the objects through the tract.

SUMMARY OF THE INVENTION

Various embodiments of the present invention may provide an examining device capable of being depleted omnidirectionally, for example to facilitate its passage through abnormal configuration of a body lumen and a method for omnidirectional depletion of the examining device. In some embodiments of the present invention the examining device may have initial dimensions for a predetermined time period and may take on final dimensions in-vivo after a predetermined time period. The final dimensions may be substantially reduced as compared to the initial dimensions. In some embodiments of the present invention the examining device may be a solid bolus substantially coated with a substantially impermeable outer coating. The solid bolus may contain one or more caps and a device body. The device body may, for example, contain filler. One or more openings in the coating may expose the bolus and/or cap to an in-vivo environment. According to an embodiment of the invention one or more of the caps may serve as a timer. The coating may be depleted of the bolus in-vivo and may be collapsed to final dimensions.

BRIEF DESCRIPTION OF THE FIGURES

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1:
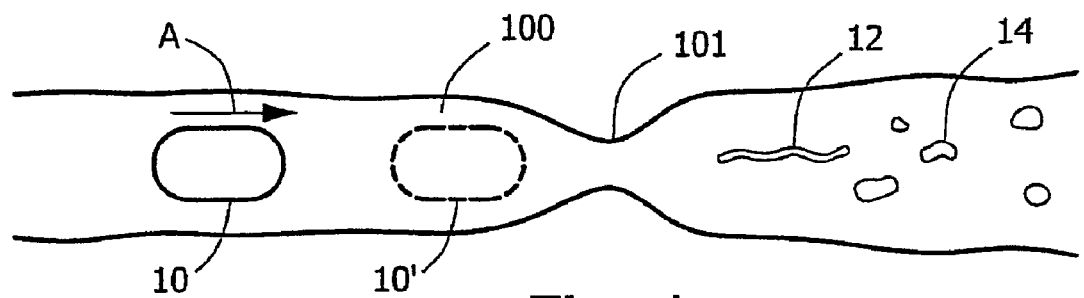
FIG. 1 is a schematic illustration of two phases of an examining device in-vivo, according to an embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where-considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

An atypical passage of an object through a body lumen or symptoms appearing after the insertion of an object into a body lumen may be indicative of an abnormal configuration of the body lumen. An examining device according to embodiments of the invention, which may, for example, examine a body lumen and/or may be an indicator of the body lumen configuration, may be designed to be depleted from its contents in-vivo and thus be safely exited from the body, independently of the configuration of the body lumen. According to one embodiment the body lumen may be the gastrointestinal (GI) tract.

Reference is now made to FIG. 1 showing a schematic illustration of the two phases of an examining device in-vivo, according to an embodiment of the invention. An examining device 10, for example, an autonomous device having initial dimensions may be inserted into a body lumen 100 and may be moved through the body lumen 100 (for example, in the direction indicated by the arrow A) actively or passively. The device 10, with initial dimensions, for example, a diameter of 1-12 mm may, for example, pass freely through the lumen 100 that may span over a given width, for example, a width of 1 mm to 10 cm, until a stricture 101 may be reached. Device 10 may pass through other body lumens and may have other suitable initial dimensions. At and/or near the stricture 101, the width may decrease such that device 10 in its initial dimensions may not be able to pass through stricture 101. In one example, stricture 101 may be a residual functioning lumen of, for example, about 2-10 mm. Strictures with other dimensions and other ranges of dimensions may be encountered by device 10. The device (now illustrated in a broken line and referred to by the numeral 10') may be unable to continue its passage through the body lumen 100 due to its dimensions, which may be larger than the dimensions of the body lumen at the stricture 101. The device 10, in its initial dimensions, may thus be blocked at the stricture 101. In some embodiments of the present invention, examining device 10 may block the opening through stricture 101. Prolonged blockage of a body lumen, for example a body lumen of the GI tract may be dangerous and/or may cause discomfort to a patient.

After a predetermined time period the device's 10 dimensions may be changed, for example, to reduce or substantially reduce its dimensions and/or volume. Typically, the predetermined time period may be set to exceed the time period that it would normally take the examining device 10 to exit the body and/or specified body lumen in a case where no strictures were encountered. In some embodiments of the present invention, the device may change its dimension in a step-like fashion after the predetermined time period so as to avoid blocking a body lumen for a prolonged period. For example, for a predetermined time period, the device 10 may substantially maintain its initial dimensions and rigidity and soon after that predetermined time period the device may take on its final dimensions. In one example, the device 10 may be depleted from its contents and thereby, for example, collapse resulting in its final dimensions 12. Omnidirectional depletion may facilitate clearing of the blockage that may be aggravated by device 10 in a near step-like fashion. In some embodiments of the present invention, depletion may take about 10-20 hours, for example 16 hours. In other embodiments of the invention, depletion may occur in a shorter or longer period of time. Final dimensions 12 may have, for example, a reduced volume and a flattened shape with a diameter substantially between 30 µm-100 mm. Other suitable ranges of final dimensions and shapes may result. In another example, device 10 may be, for example, disintegrate or degrade into several small sections or particles 14, each of which may be approximately less than, for example, 0.5 wide. Other suitable ranges of final dimensions may be implemented that may be more or less than 0.5 wide. In other embodiments of the present invention device 10 may have final dimensions that may be any combination of final dimensions 12 and 14. The device in its final dimensions 12 and/or 14 may pass through the stricture 101 and may, for example, exit the body. In alternate embodiments, the dimensions or shape of the body lumen 100 may be different and the device 10 may change in other manners, to other dimensions or shapes. For example, the device need not be broken into more than one section.

In another embodiment of the invention, the examining device 10 may be used to simulate the passage of another in-vivo device, such as a diagnostic and/or therapeutic device, through a body lumen, for example, an autonomous diagnostic and/or therapeutic device. In this case, obtaining information on the passage of the examining device through the body lumen may be advantageous in designing a specific in-vivo device or in determining whether a certain in-vivo device may be safely used on a patient. In one embodiment, different sized and shaped examining devices 10 according to an embodiment of the invention may be passed through a body lumen to determine the most suitable size and shape for an in-vivo device to be freely and safely passed through the same lumen.

In one embodiment of the present invention, the initial dimensions may be typically determined in accordance with the known anatomy and/or physiology of a body lumen. In its final phase the dimensions of the examining device may be typically substantially smaller and its shape possibly changed such that it may freely pass through the body lumen even if the lumen dimensions may be smaller than expected in accordance with the known anatomy and/or physiology of the body lumen. Proceeding from an initial phase to a final phase of the examining device, may, for example, be promoted by endoluminal conditions or may be externally controlled.

Passing of the examining device through a body lumen may, for example, simulate the passage of the target in-vivo device through that body lumen and thus a safe method of indication may be provided as to the transferability of the target in-vivo device in the body lumen.

Typically the examining device 10 may include at least two phases, an initial phase in which the examining device's (10) dimensions approximately resemble the dimensions of a target in-vivo device and a final phase in which the dimensions of the examining device 10 may be changed so as to enable the examining device 10 to pass through unexpected configurations of body lumen and/or abnormally configured body lumens. In other embodiments more than two phases may be implemented. In some embodiments of the present invention, the dimensions of examining device 10 may be changed, by depleting part and/or all of internal contents of the examining device 10 and changing the dimensions of an external portion of the examining device 10 to final dimensions.

In another embodiment of the present invention, the device 10 may be shaped, sized or have dimensions substantially similar to an autonomous ingestible imaging device for purposes of imaging the GI tract The device 10 may be safely passed through the GI tract, to test the transferability of such a diagnostic or therapeutic device through the GI tract, while its progression may be monitored and/or the phase the device 10 is in may be detected as may be described herein. In the event the device 10 may not traverse a section of the lumen, its shape or dimensions may change to allow passage. The examining device 10 may be, for example, capsule shaped, shaped similar to and containing components similar to the ingestible capsule described in U.S. Pat. No. 5,604,531, entitled "An in-vivo video camera system" which is hereby incorporated in its entirety by reference, Publication Number WO 01/65995, also assigned to the common assignee of the present application and incorporated herein by reference, and/or similar in shape and size to other pills, tables capsules and the like, known in the art.

In one embodiment, a capsule shaped examining device 10 possibly having, for example, initial dimensions of approximately 11 mm×26 mm may be used to test the GI tract. Other suitable dimensions may be used. The device 10 may be swallowed or otherwise placed or inserted in the GI tract (by an endoscope, for example) and may be passively moved through the GI tract due to peristalsis of the GI tract, until it may be naturally excreted from the body. In other embodiments of the present invention, device 10 may be actively advanced through the GI tract.

Figure 2:
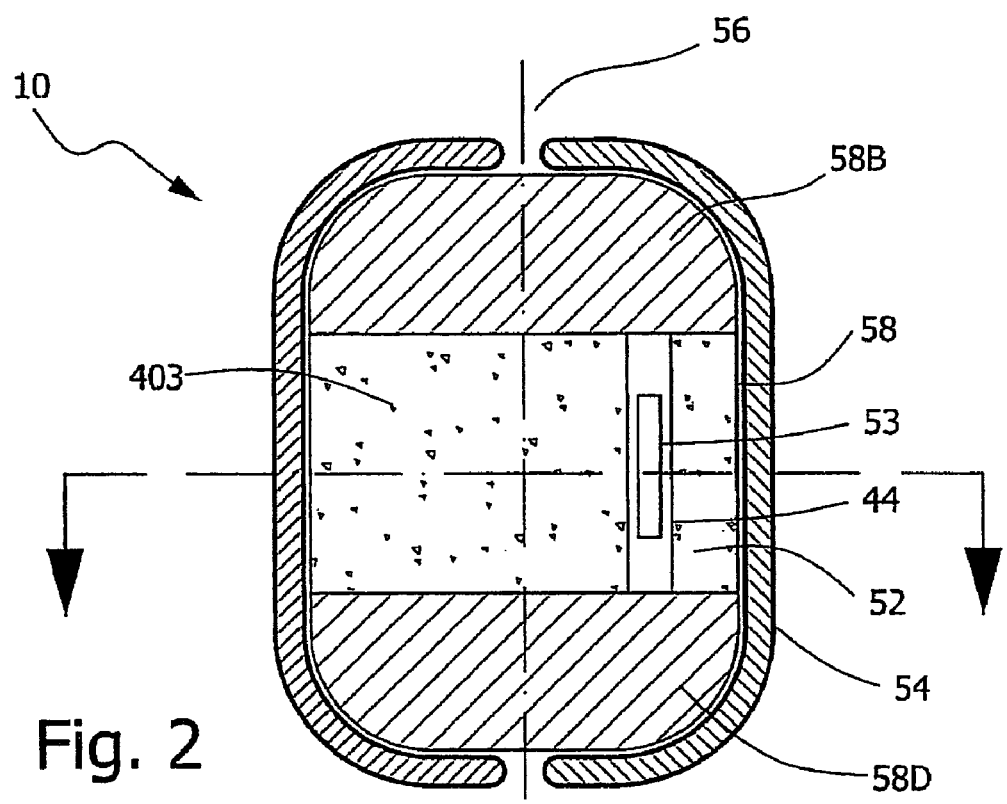
FIG. 2 is a schematic illustration of a front cross sectional view of an examining device according to an embodiment of the present invention.

Reference is now made to FIG. 2 schematically illustrating a front cross sectional view of an examining device according to some embodiments of the present invention. According to an embodiment of the present invention, device 10 may be a bolus 58 capable of being disintegrated that may typically include a device body with, for example, filler 52 sandwiched between two caps 58B and 58D that may be substantially enclosed within a coating 54, for example a pliable coating. In other embodiments of the present invention, more or less than two caps 58B and 58D may be used and filler 52 may not be sandwiched between two caps 58B and 58D. The coating 54 may typically be a layer or a plurality of layers of, for example, substantially impermeable or slightly permeable material or combination of materials, which may be essentially durable (e.g., may not corrode or disintegrate) under in-vivo conditions. The bolus 58 may typically be composed and/or fabricated from an eroding and/or dissolvable material. One or more openings, aperture, and/or windows 56 in coating 54 may partially expose bolus 58 to the surrounding environment and may allow, for example, in-vivo fluids to cause disintegration (e.g. erosion) of the caps 58B and 58D and depletion of device 10 over a predefined time period. Typically, an opening may be for example a circular opening with a diameter of approximately 1-10 mm and an area of approximately 0.5 to 100 mm². Other suitable openings with other shapes and sizes may be used as well. Erosion of caps 58B and 58D may be dependant on parameters, such as, the size of window 56, the number of windows 56, the direction that each window 56 faces with respect to the body lumen through which device 10 may be traveling, the properties of the material fabricating caps 58B and 58D, the dimensions and/or volume of the caps 58B and 58D, and the density of caps 58B and 58D. Other conditions may influence the erosion time of each of the caps 58B and 58D and the depletion time of device 10. The caps 58B and 58D may be designed to erode at a desired predetermined time period. For example, the dimensions, material, and density of the material packaged may be set to meet the requirement of maintaining the external dimensions of the examining device 10 for a predetermined time period and subsequent to the elapsed predetermined time period, depleting the contents of the examining device 10 in a near step-like fashion. Typically, caps 58B and 58D may act as a timer for the disintegration of device 10. More than one aperture and/or more than one window 56 facing in more than one-direction, for example substantially opposite directions, may allow bidirectional or omni-directional depletion of device 10.

According to an embodiment of the invention, coating 54 has initial dimensions that are changeable to final dimensions and the bolus 58 comprises particles that are of final dimensions. Final dimensions enable passage of the device in a body lumen configuration that is not enabled by the initial dimensions. Partial or full depletion of coating 54 from bolus 58 may initiate the changes in the dimension of coating 54. For example a volume that coating 54 encloses may be directly related to the volume of bolus 58 that coating 54 encompasses. Upon depletion of the contents encompassed by coating 54, the initial dimensions of coating 54 may change to final dimensions in a near step-like fashion. The pliable characteristic of coating 54 may enable coating 54 to take on final dimensions that are substantially reduced form the initial dimensions. As such, coating 54 may pass through a strictured body lumen while intact.

In some embodiments of the present invention, a monitoring mechanism, for example, an ID tag 53 may be included within examining device 10, for example, to allow monitoring of the presence of device 10 in a specified location and/or in-vivo. In other embodiments of the present invention, a traceable material 403, for example a radio opaque material may be used to monitor the presence of examining device 10 in a specified location and/or in-vivo. In yet other embodiments, other suitable methods or a combination of more than one method maybe used to monitor device 10. In other embodiments of the present invention, device 10 need not be monitored.

In one embodiment of the present invention, caps 58B and 58D may typically be fabricated and/or composed from a hydrophobic material, for example, a hydrophobic wax containing microencapsulated hydrophobic material, or from a combination of hydrophobic and hydrophilic material. Non-limiting examples of materials that may be suitable for cap 58B and 58D may, for example, include, Compritol 888, Avicel PH 200, Lactose anhydr., PVP K-90, or a combination of more than one material may be used. In another embodiment of the present invention, the cap may be composed and/or fabricated from other synthetic waxes or, for example, lipophilic material of plant origin or hydrocarbons (simple and/or complex). Other suitable materials may be used. According to one embodiment of the present invention, the hydrophobic material may include micro-particles to facilitate flow of in-vivo fluids into the cap and to facilitate the disintegration of the cap at a given rate. A system that may be suitable to use in an embodiment of the present invention may be a system of nano-particles, for example, formed of a solid hydrophobic inner core and a cationic exterior. The nano-particles may be encapsulated in micro-capsules. In one embodiment the nano-particles may be encapsulated In moisture sensitive micro-capsules. Such systems may be produced, for example, by Salvona, USA. In some embodiments of the present invention, caps 58B and 58D may be pressed into a desired shape and dimensions by known methods. Fabricating caps 58B and 58D by pressing of synthetic material, e.g. Compritol 888, Avicel PH 200, Lactose anhydr., and/or PVP K-90, may result in less or no expanding or swelling of the cap when coming in contact with in-vivo fluids that may otherwise occur when using natural waxes or derivatives of natural waxes. In some embodiments of the present invention, the cap may be composed by a combination of hydrophobic and hydrophilic material and the ratio between the hydrophobic and hydrophilic material may determine and/or be related to the erosion rate of the cap. For example, a composition with a relatively higher ratio of hydrophobic material as compared to hydrophilic material, e.g. 1:3 hydrophobic/hydrophilic, may erode at a slower rate compared to a composition with a relatively lower ratio of hydrophobic material as compared to hydrophilic material, e.g. 1:12 hydrophobic/hydrophilic. In one example, the cap may be fabricated from layers of more than one or more than one combination of hydrophobic materials. In another example the cap may be fabricated from layers of material packaged with different densities. For example, to maintain the outer dimensions of the examining device intact for the predetermined time period, an outer layer of the cap may, for example, be pressed and/or packaged with a higher density than the internal layers so that erosion rate of in the inner portion of the cap may be higher than the erosion rate in the outer surface of the cap. Other suitable methods of fabricating caps 58B and 58D and/or eroding caps 58B and 58D while maintaining the outer dimensions of device 10 for a predetermined time period may be used. Typically but not necessarily, one or more caps 58B and 58D may have substantially similar dimensions. In some embodiments of the invention, one or more caps 58B and 58D may have different dimensions and/or configuration. In one embodiment of the present invention, in a device of about 11 mm×26 mm, caps 58B and 58D may have a substantially dome shape with a longitudinal length of approximately 4-6 mm. Other suitable sizes may be used and each of the caps 58B and 58D may have a different length or geometry. Typically, but not necessarily cap 58B and 58D and device body and/or filler 52 may be made of different materials.

Filler 52 may typically be of any suitable biodegradable or dissolvable material, for example any suitable excipient, e.g. lactose, powdered sugar, etc. Typically, filler 52 may be strong enough to withstand endo-luminal pressure. The filler 52 may also contain adhesives and other fillers to, for example, further provide mechanical stability to the device. Other suitable materials may be used. Filler 52 may be pressed into a desired shape and dimensions by known methods. In one embodiment of the present invention, filler 52 may be cylindrical with dimensions approximating 12-14 mm in length and 9-12 mm in diameter. Other suitable dimensions may be used. Caps 58B and 58D may be joined and/or glued to filler 52 with an adhesive, for example, a biocompatible adhesive, e.g. UV glue. Other suitable methods of joining caps 58B and 58D to filler 52 may be used. In other examples cap 58B and 58D may be joined and/or affixed to filler 52 by packaging and/or coating, for example, coating with coating 54. Other suitable methods may be used Typically, the outer coating 54 may be a thinner layer than the internal bolus 58. According to some embodiments, the outer coating 54 may be designed to impart mechanical strength to the device and keep the device shape and dimensions constant throughout the initial phase (and/or the predetermined period) of the device. The coating may also serve as a barrier between the internal filler 52 and the surrounding environment, e.g. the endo-luminal environment. Typically, coating 54 may be a thin layer of impermeable polymer, for example, a thin layer of Parylene C, for example, an 8-10 μm layer of Parylene C. Other suitable coatings and coating methods may be used. Typically, upon depletion of bolus 58 through window 56, coating 54, which may be pliable, may change to final dimensions (e.g. reduced and/or collapsed dimensions). In some embodiments of the invention, coating 54 may collapse to final dimensions including a width of, for example, 30 μm-0.5 mm.

In one embodiment of the present invention, device 10 may also include a monitoring mechanism, for example, an ID tag 53 e.g. radioactive, color or magnetic tag or an electronic ID tag (e.g., an RFID tag) within the bolus 58 or filler 52. Other monitoring mechanisms or beacon device may be used. ID tag 53 may be, for example, a radio-frequency (RF) ID tag. In one embodiment of the invention, the tag may include two components: a metal coil which may act as a two-way antenna and a silicon chip that may be activated by energy received from an outside source, and when activated may send back a single identification signal which may be picked up by an external pick up device, for example a radio frequency scanner. Typically, these components may be encapsulated in, for example, a glass casing. In one example, the glass casing may be re-encapsulated with for example medical grade polyurethane as a protective jacket. Other suitable methods for detecting the presence of the examining device may be implemented and other suitable ID tags 53 may be used. One exemplary dimension of an ID tag 53 may be 2-3 mm in diameter and 12-15 mm in length. Other suitable dimensions may be used.

Figure 3:
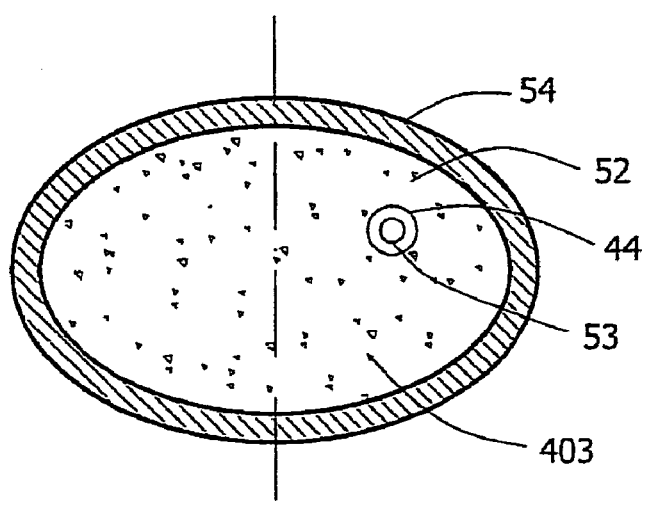
FIG. 3 is a schematic illustration of a top cross sectional view of an examining device according to an embodiment of the present invention.

Reference is now made to FIG. 3 showing a top cross sectional schematic illustration of device 10 where an ID tag 53 may be included in filler 52. In one embodiment of the present invention, a bore 44 may be made within filler 52 so that an ID tag 53 may be inserted through it. In one embodiment of the present invention, bore 44 may have dimensions of 2 mm in diameter and 13 mm in length. Other suitable dimensions may be used. Other suitable methods may be used for incorporating an ID tag within device 10.

In some embodiments of the present invention, a material 403 providing, for example, a radio opaque effect may be included within bolus 58, e.g. within filler 52. An example of a suitable material may be for example barium sulphate powder. Other suitable materials may be mixed into the filling for easily monitoring of device 10 by, for example, x-ray. In one embodiment of the present invention filler 52 may contain 10% barium sulphate powder. Other suitable concentrations and other suitable detectable materials may be used. The device 10 with ID tag 53 or traceable material 403 may be monitored, for example, by using a reader such as a suitable reader provided by Trovan Ltd. UK. Other methods of monitoring may be implemented. The tag may be the tags described herein, such as a radioactive marker, a magnetic device, or a radio based tag.

In one embodiment of the present invention, the device 10 may also include an examining mechanism, such as a thermometer, pH meter, etc., for examining endo-luminal conditions, or other sensing devices such as an imaging device. In another embodiment of the present invention, filler 52 may contain one or more medical drugs, for example, that may be released, for example in an abnormally configured lumen during depletion of filler 52. In some embodiments of the present invention, an effervescent component may be added to filler 52 to expedite the depletion of filler 52.

Device 10 may be designed to substantially maintain its outer dimensions for a predetermined period of time after which surface erosion through window 56 due to in-vivo fluids, for example, gastric and/or GI fluids may disintegrate and/or erode the caps 58B and 58D and the in-vivo fluids may penetrate the body of device 10 where they dissolve the filler 52, leaving behind the pliable coating and the tag 53. In some embodiments of the present invention, the change in dimension may occur in a near step-like fashion.

In some embodiments of the present invention, the rate of erosion of caps 58B and 58D through windows 56 may not be uniform. In one example, device 10 may block the stricture 101 and little or no fluid may come in contact with the downstream facing cap 58D. The exposure to in-vivo fluids on the downstream side of the device 10 may be significantly reduced such that, for example, erosion of cap 58D may come to a near halt. In other embodiments of the present invention, exposure of each of the caps 58B and 58D may differ due to other conditions. Omnidirectional exposure to in-vivo fluid may ensure depletion of device 10 after a predetermined period elapsed and may accelerate the depletion of device 10 after the predetermined period elapsed. For example, exposure of in-vivo fluids may in general be greater for a cap 58B facing upstream as compared to another cap 58D facing downstream. In other embodiments of the present invention, non-uniform erosion of each of the caps 58B and 58D may be due to other factors, for example, each of caps 58B and 58D may be fabricated and/or composed with different materials, in different sizes, and/or shapes so that they may erode over different time periods. In yet other embodiments of the present invention, erosion of caps 58B and 58D may be due to other factors besides and/or in addition to exposure to in-vivo fluids.

In a method according to an embodiment of the present invention an examining device may examine endo-luminal conditions, or test the configuration of a body lumen, detect configurational abnormalities in a body lumen and/or simulate the passage of an in-vivo device in a body lumen while no long term obstruction of the body lumen may be posed. According to an embodiment of the invention, an examining device in its initial phase may include dimensions such that it may pass through a typically healthy body lumen and/or give a good approximation of the passage of an in-vivo device in the body lumen. In its final phase the examining device's dimensions may be changed (typically reduced, although other changes are contemplated) so that it may pass through an abnormally configured body lumen where the examining device in its initial phase could not, because of its dimensions.

In case the body lumen is of unexpected dimensions (wherein the expected dimensions are based, for example on the known or typical anatomy and/or physiology of the body lumen) or in case of a stricture or any other configurational abnormality in the body lumen, the examining device in its initial dimensions may be blocked from continuing its typical or expected passage in the body lumen. After a predetermined time the examining device's dimensions may be changed such that the examining device, in its final phase, typically depleted of its former contents and typically of degraded or reduced form, will not be blocked from passing even through a smaller or abnormally configured body lumen.

If no clinical or configurational abnormalities are present in the body lumen the examining device's passage through the body lumen may be typical and the examining device may pass through the body lumen and exits the body while it may still maintain its initial dimensions. However, in a case in which the body lumen may be abnormally configured (e.g., there is a stricture) or if there is a clinical problem (e.g., slow or no motility in the gastro intestinal tract) the examining device may be held back in the body lumen and reaches its final dimensions while in the body lumen. The degraded or reduced device may be able to continue its passage through the body lumen to eventually exit the body. It will thus be appreciated that the device and method of the invention may be utilized to detect clinical and/or configurational abnormalities in body lumens through which the device may be passed and exited, such as the GI tract, the urogenital tract, the reproductive tract, the oral-nasal cavity, etc, or a portion of any of these lumens.

A person skilled in the art may easily adjust the specific design of the examining device and the predetermined time period between an initial and final phase of the examining device to be applicable to a specific body lumen having specific and known anatomy and physiology.

Figure 4A:
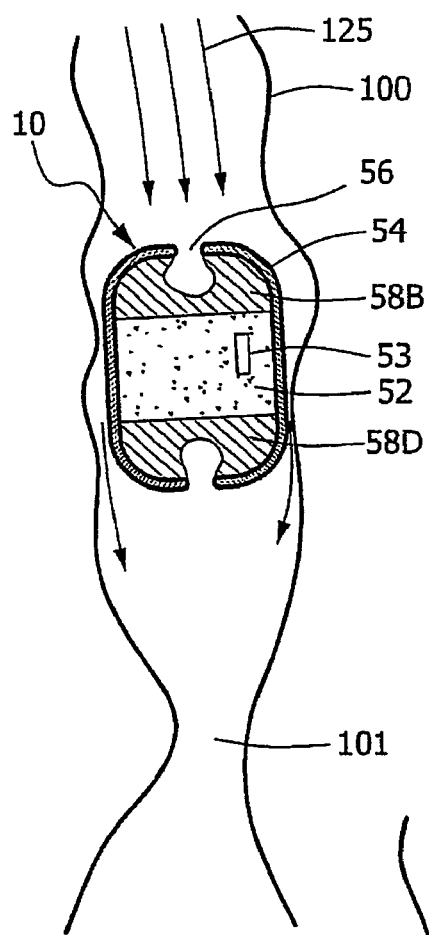
FIGS. 4A, 4B, and 4C are consecutive schematic illustrations of a progression of an examining device passing through a stricture of a body lumen according to embodiments of the present invention.
Figure 4B:
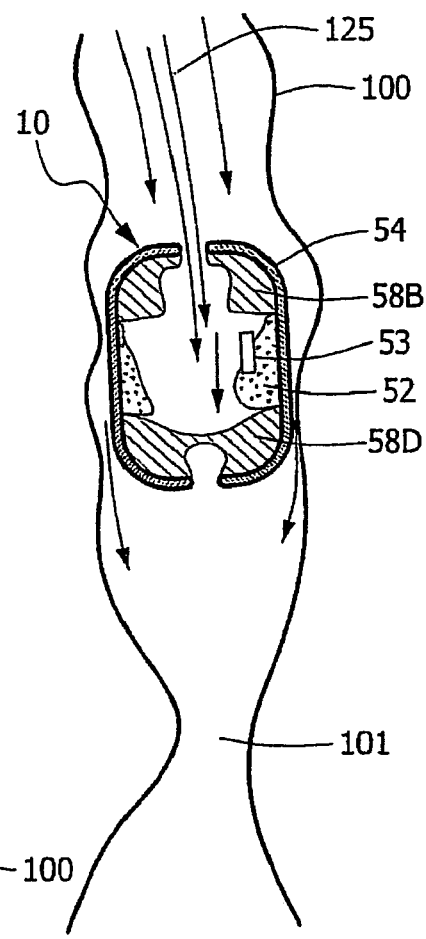
Figure 4C:
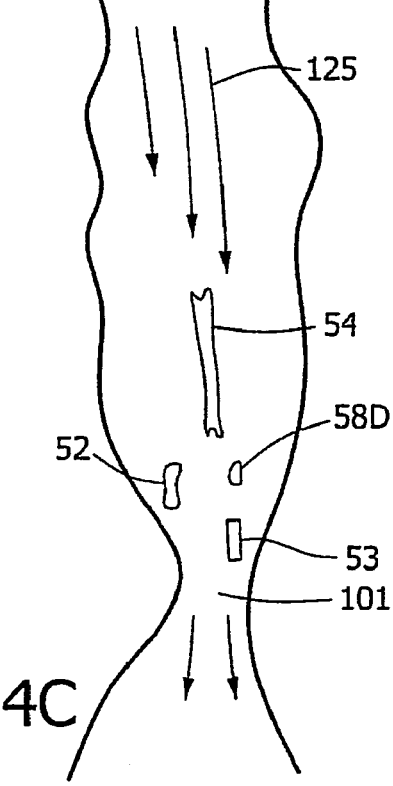

Reference is now made to FIG. 4A, 4B and 4C showing consecutive schematic illustrations of a progression of an examining device 10 passing through a stricture 101 of a body lumen 100 according to an embodiment of the present invention. Reference is now made to FIG. 4A showing a front cross sectional schematic illustration of an examining device 10 traveling through body lumen 100 and approaching an area with a stricture 101. During travel through body lumen 100, contact with in-vivo fluids 125 through windows 56 may promote erosion of caps 58B and 58D. For a predetermined period, the erosion of caps 58B and 58D and/or the omnidirectional depletion of device 10 may continue with out compromising the rigidity and outer dimensions of device 10.

In some embodiments of the present invention, erosion of caps 58B and 58D may be a function on the degree of contact caps 58B and 58D may have with the surrounding in-vivo fluids. For example, the orientation of examining device 10 with respect to the body lumen may result in one of its caps, for example cap 58B, having greater exposure to in-vivo fluids as compared to another of its cap 58D. For example, a first cap 58B facing an upstream direction may have more exposure to in-vivo fluids as compared to second cap 58D facing in a downstream direction. As such, the first cap 58B facing in the upstream direction may erode within a shorter time period as compared to the second cap 58D facing the downstream direction. Including two or more caps 58B and 58D in device 10 may, in some embodiments of the present invention, ensure that a desired change in dimension may take place at a predetermined time period, even if one of the caps 58B or 58D may have had insufficient exposure to in-vivo fluids due to in-vivo conditions. Omnidirectional depletion of device 10 may allow for accelerated depletion of device 10 and/or coating 54, typically, in a step-like fashion at the termination of the predetermined period.

In another example, when approaching an area with a stricture, device 10 may, for example, block passage of in-vivo fluid and one of the caps, for example cap 58D possibly facing the direction of the stricture may experience little or no contact with in-vivo fluids. As such, it may be possible that the erosion of caps 58D may be temporarily halted, nearly halted, and/or slowed down. Omnidirection depletion of coating 54 enables the passage of device 10 regardless of the orientation of device 10 with respect to the body lumen 100 and/or regardless of the orientation of device 10 with respect to the stricture 101.

Reference is now made to FIG. 4B, showing a device 10 with a substantially eroded cap 58B. In-vivo fluids may diffuse or flow in through window 56, eroding, for example, cap 58B enough to create an opening to filler 52. The filler 52 may typically be made of a material that may be faster to dissolve than the material composing the cap 58B and 58D. Exposure of filler 52 to in-vivo fluids, may facilitate rapid depletion of filler 52 such that dimensions of device 10 may be substantially altered. In some embodiments of the present invention, filler 52 may be substantially dissolved before cap 58D may have substantially eroded. As such, in-vivo fluids may expose cap 58D through the filler 52 side and erosion of cap 58D may occur from both sides, accelerating the erosion of cap 58D, so that device 10 may successfully pass through stricture 101 and relieve blockage that may have been temporarily aggravated by device 10. In one embodiment of the present invention, erosion of cap 58D may occur mainly from the upstream direction due to lack of in-vivo fluids in the downstream direction. In other embodiments of the present invention, device 10 may be able to pass through stricture 101 during depletion of filler 52 and before complete erosion of cap 58D.

Reference is now made to FIG. 4C. Erosion of cap 58B, filler 52 and cap 58D may, for example, lead to pliable coating 54 disengaging at least partially from the material that it may be coating and in its new smaller and/or collapsed dimensions may pass easily through stricture 101. ID tag 53 may be released from filler 52 and also pass through stricture 101. In other embodiments, fragments of filler 52 and caps 58B and 58D may pass through stricture 101 while still in the process of disintegration and/or erosion. In some embodiments of the present invention, rapid depletion of device 10 (after the predetermined time period may have elapsed) may be desired so as to minimize any discomfort to a patient (for example, undergoing an examination with examining device 10) that may be caused by further blockage of a strictured area 101 by the examining device 10. Erosion of caps 58B and 58D from both the upstream and downstream direction may accelerate the change in dimension of examining device 10 so that it may vacate the pathological and/or strictured area without unnecessary delay.

A health professional may monitor (e.g. with known monitoring devices) the passage of device 10 through a body lumen to determine the presence of abnormal body lumen configurations. The presence of device 10 or the contents of device 10 (e.g. ID tag 53, material 403) in-vivo for less than the predetermined time may be indication that no abnormal body lumen configurations were encountered. Detection of device 10 or the contents of device 10 (e.g. ID tag 53, material 403) in-vivo substantially after the predetermined time may be indication that abnormal body lumen configurations were encountered. In some embodiments of the present invention the predetermined time period may be in the order of one hundred hours. In other embodiments a period of approximately forty to seventy hours may be used. In still alternate embodiments, other time limits may be used, and examining devices for other body lumens may be designed in accordance with the specific body lumen having specific and known anatomy and physiology.

In one embodiment of the present invention, a health professional may detect the presence of device 10 in a defined area in a body lumen to determine the presence of abnormal body lumen configurations. The presence of device 10 or the contents of device 10 (e.g. ID tag 53, material 403) in a defined area for less than the predetermined time may be indication that no abnormal body lumen configurations were encountered. The presence of device 10 or the contents of device 10 (e.g. ID tag 53, material 403) in a defined area for more than the predetermined time may be indication that abnormal body lumen configurations were encountered.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. An in vivo examining device comprising:
   a device body;
   two erodible caps;
   a substantially impermeable outer coating for substantially covering at least the two caps, said coating comprising at least two openings, wherein each of said two caps is exposed by at least one of said two openings;
   wherein the device body is covered by the coating and comprises filler sandwiched between the two caps.

2. The device according to claim 1 wherein the caps include a combination of hydrophobic and hydrophilic materials.

3. The device according to claim 2 wherein the hydrophobic material is selected from a group consisting of: glyceryl behenate and microcrystalline cellulose, and the hydrophilic material is selected from a group consisting of: anhydrous lactose and polyvinylpyrrolidone.

4. The device according to claim 1 wherein the coating is durable under in-vivo conditions.

5. The device according to claim 1 wherein the coating is a pliable coating.

6. The device according to claim 1 wherein the coating includes Parylene C.

7. The device according to claim 1 wherein the coating is configured for taking on substantially reduced dimensions in-vivo after a predetermined time period.

8. The device according to claim 1 wherein the filler includes at least a dissolvable material.

9. The device according to claim 1 wherein the filler includes at least one material selected from a group consisting of: lactose and powdered sugar.

10. The device according to claim 1 wherein the device body comprises a monitoring mechanism.

11. The device according to claim 10 wherein the device body comprises an RF ID tag.

12. The device according to claim 1 wherein the device body includes at least barium sulphate.

13. The device according to claim 1 wherein each of the two caps is glued to the device body.

14. The device according to claim 13 wherein each of the two caps is glued to the device body with UV glue.

15. The device according to claim 1 comprising a monitoring mechanism.

16. The device according to claim 15 comprising an RF ID tag.

17. The device according to claim 1 wherein the device includes barium sulphate.

18. The device according to claim 1 wherein the area of each of the openings is 0.5 mm$^2$ to 100 mm$^2$.

19. A method of use of an examining device within a body lumen, the method comprising:
   providing an examining device with a body comprising a dissolvable filler material and two erodible caps, the examining device configured for being depleted omni-directionally after a predetermined time period; and
   inserting said examining device into said body lumen;
   wherein the dimension of said examining device changes to final dimensions after the predetermined time period in a step-like fashion, wherein final dimensions of the device include a width of between 30 µm and 0.5 mm.

20. The method according to claim 19 wherein the body lumen is a lumen of a GI tract.

21. The method according to claim 19 wherein the examining device is capsule shaped.

22. The method according to claim 19 comprising coating the examining device with a substantially impermeable outer coating.

23. The method according to claim 21 comprising providing an opening through the coating to expose the cap.

24. The method according to claim 21 comprising providing a first opening through the coating facing an upstream direction; a second opening through the coating facing a downstream direction.

25. The method according to claim 19 comprising depleting the examining device in the upstream and downstream direction.

26. The method according to claim 19 wherein the predetermined time period is approximately between forty and one hundred hours.

27. The method according to claim 19 comprising monitoring the examining device.

* * * * *

UNITED STATES PATENT AND TRADEMARK OFFICE
CERTIFICATE OF CORRECTION

PATENT NO. : 7,585,283 B2
APPLICATION NO. : 10/988614
DATED : September 8, 2009
INVENTOR(S) : Kraizer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1230 days.

Signed and Sealed this

Fourteenth Day of September, 2010

David J. Kappos
*Director of the United States Patent and Trademark Office*